United States Patent [19]
Lares et al.

[11] Patent Number: 5,743,731
[45] Date of Patent: Apr. 28, 1998

[54] INSTRUMENT HOLDER WITH INTEGRATED CAMERA CAPABILITY AND INTERCHANGEABLE INSTRUMENT TIPS

[75] Inventors: Craig J. Lares; Ravi Pathmanabhan; Jason E. Orgain, all of Chico, Calif.

[73] Assignee: Lares Research, Chico, Calif.

[21] Appl. No.: 707,050

[22] Filed: Aug. 30, 1996

Related U.S. Application Data

[63] Continuation-in-part of Ser. No. 487,364, Jun. 7, 1995, Pat. No. 5,634,790.

[51] Int. Cl.$^6$ .............................. A61C 1/00; A61B 1/00
[52] U.S. Cl. .............................. 433/29; 600/160
[58] Field of Search .................... 433/29, 25; 600/104, 600/109, 112, 136, 156, 157, 160, 169, 127, 129, 137, 182

[56] References Cited

U.S. PATENT DOCUMENTS

| | | | |
|---|---|---|---|
| 2,643,456 | 6/1953 | Maurer et al. | 433/29 X |
| 4,171,572 | 10/1979 | Nash . | |
| 4,398,885 | 8/1983 | Loge et al. | 433/29 X |
| 4,403,956 | 9/1983 | Makanishi | 433/29 |
| 4,431,412 | 2/1984 | Lares et al. . | |
| 4,519,780 | 5/1985 | Strohmaier et al. | 433/29 |
| 4,521,189 | 6/1985 | Lares et al. . | |
| 4,534,734 | 8/1985 | Lares . | |
| 4,614,498 | 9/1986 | Vaccaro . | |
| 4,838,246 | 6/1989 | Hahn et al. | 600/157 X |
| 4,966,552 | 10/1990 | Gonser . | |
| 5,003,432 | 3/1991 | Mandy . | |
| 5,052,924 | 10/1991 | Berg | 433/29 |
| 5,178,536 | 1/1993 | Werly et al. . | |
| 5,512,036 | 4/1996 | Tamburrino et al. | 433/29 X |
| 5,634,790 | 6/1997 | Pathmanabhan et al. | 433/29 |

OTHER PUBLICATIONS

The New 430 Series High Speed Handpieces, Star Dental Division of DEN–TAL–EZ, Inc., 1995.

*Primary Examiner*—Jeffrey A. Smith
*Attorney, Agent, or Firm*—John P. O'Banion

[57] ABSTRACT

A dental/medical instrument holder with an internal imaging or video system wherein the body of the instrument is readily detachable from a connector portion. The instrument holder preferably contains a swivel feature which allows the body to swivel or rotate 360 degrees relative to the connector, and any hoses or cables attached to the connector, while the instrument is in use. The body of the instrument contains a collet or other feature which allows reversible attachment of various instrument tips. Illumination is provided to the instrument tip and adjacent work area, and images therefrom are transferred to an imaging system which includes a CCD camera within the instrument holder.

17 Claims, 6 Drawing Sheets

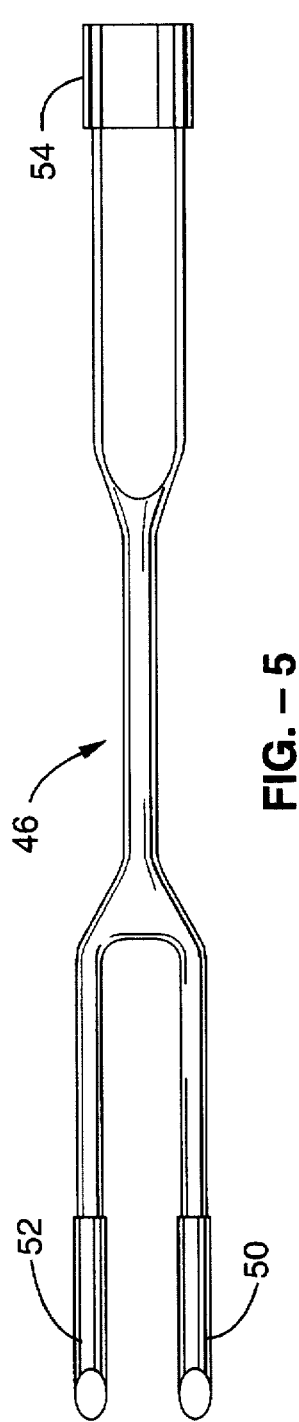
FIG. -5
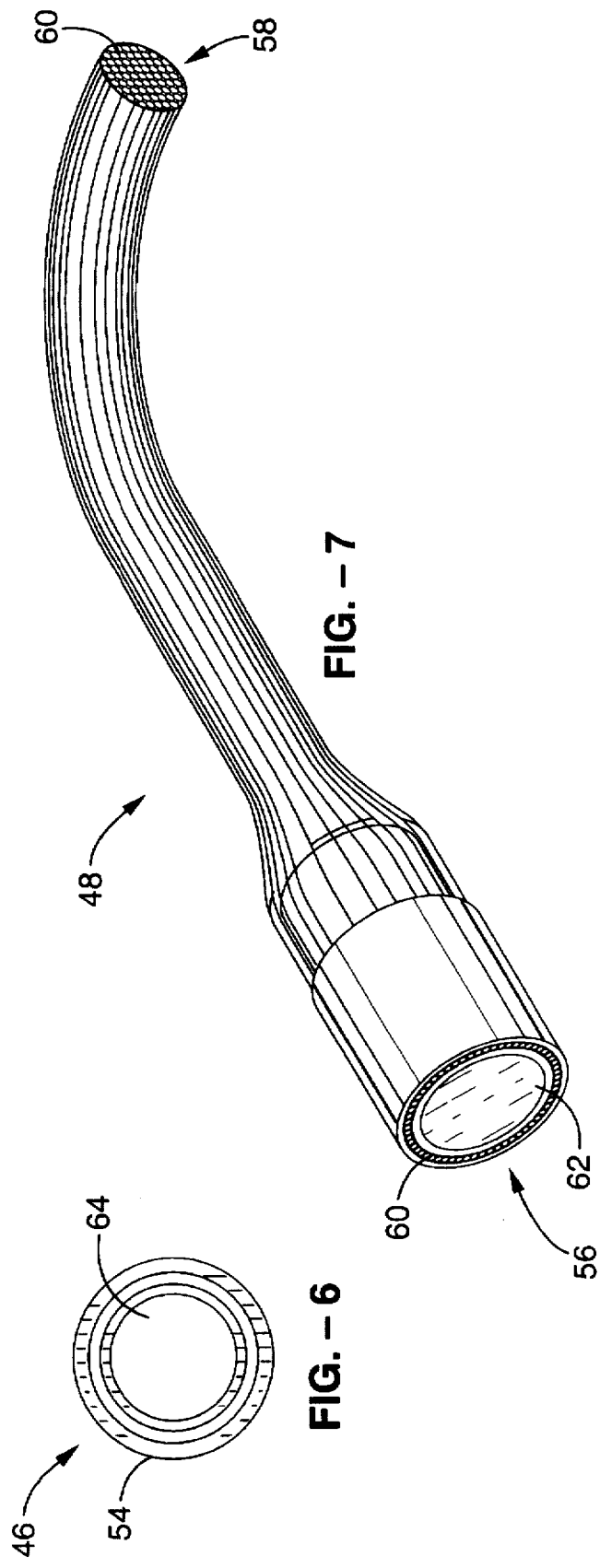
FIG. -7
FIG. -6

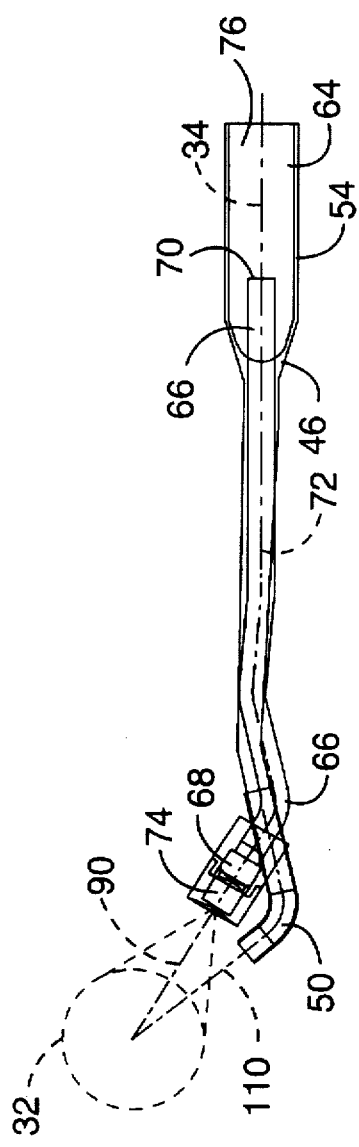

INSTRUMENT HOLDER WITH INTEGRATED CAMERA CAPABILITY AND INTERCHANGEABLE INSTRUMENT TIPS

CROSS-REFERENCE TO RELATED APPLICATIONS

This application is a continuation-in-part of application Ser. No. 08/487,364, filed on Jun. 7, 1995, now U.S. Pat. No. 5,634,790.

BACKGROUND OF THE INVENTION

1. Field of the Invention

The present invention pertains generally to dental and medical instruments with imaging capability, and more particularly to a dental and/or medical instrument with integrated intra-oral or intra-cavity imaging which provides for use of interchangeable instrument tips.

2. Description of the Background Art

Dentists frequently experience difficulty in seeing dental operations or other procedures carried out in portions of the oral cavity. A multitude of intricate procedures are carried out on patients' teeth which require dentists to see and keep track of minute details. For example, they must see geometries (parallelism, undercuts, margins, etc.) of dental preparations as well as the effects of their work as it is performed. Similarly, physicians and other medical personnel similarly must perform procedures in areas which are difficult to see due to tissue or organs blocking the physician's line of sight. Failure to see clearly and precisely may result in improper performance of a procedure or result in an excessive amount of time being required to carry out the procedure. The inability to see easily and clearly additionally results in stress and fatigue for dentists and physicians.

Traditionally, dentists have employed small mirrors mounted on handles in order to view the area of a dental operation which would otherwise not be visible. The use of mirrors, however, is difficult and does not always provide a clear view of the operating area. Therefore, dentists have shown great desire to solve the problem of seeing their work clearly in the oral cavity. In order to improve visualization of work areas, dentists have invested heavily in dental drills with fiber optic lighting, and in magnification/lighting loupe headsets to get additional light and magnification of the work area.

More recently, the advent of dental drills with built-in intra-oral camera or imaging capability has provided for magnification of the work area of dental operations, allowed viewing of the work area on a monitor or other display, and provided a field of vision which automatically follows the tip of the bur or tool. The imaging capability accompanying dental handpieces has eliminated the need for a mirror while drilling in many locations. In addition, ergonomics are improved by allowing the dentist to sit upright while viewing a magnified image of the work site, reducing bodily stress and fatigue.

While imaging capability has been incorporated into high and low-speed dental drills, there has been no integration of intra-oral imaging or camera capability into fixed or non-rotary dental instruments such as picks, probes, explorers, scrapers, scalers, etc. In using such traditional non-powered hand instruments, dentists still must resort to viewing work areas through a mirror, resulting in the traditional problems of inaccuracy, excessive time consumption, and stress and fatigue.

Accordingly, there is a need for a dental and/or medical instrument holder with integrated imaging capability which provides for detachable and interchangeable instrument tips. The present invention satisfies these needs, as well as others, and generally overcomes the deficiencies present in the background art.

SUMMARY OF THE INVENTION

The present invention is an instrument holder apparatus which extends the benefits associated with dental drills with integrated intra-oral camera capability to traditional non-powered hand instruments used during most dental procedures. In general terms, the invention comprises a generally elongated body or handle having a working end, means for reversibly attaching a dental or medical instrument tip or other tool to the working end, and a generally elongated connector which is detachable from the body. The connector may comprise the same connector used for connection of imaging dental handpieces to supply lines. The body and connector are detachably coupled, and preferably include at their point of coupling a swivel means which provides for rotation of the body and connector relative to each other. Included within the body and connector is an illumination transferring means for transferring light from a light source associated with the connector to the work area adjacent to the instrument tip. The body also includes an image transferring means for transferring images to an image detection means located either internally or externally to the connector. The optical train of the imaging and illumination transferring means are preferably similar or identical to that used with imaging dental drill devices. Preferably, pressurized water and pressurized air means for delivering air and water to the instrument tip and work area are included with the body and connector.

The reversible attachment means preferably comprises a collet, chuck, or like feature having a socket, collar, or similar hardware which can reversibly receive and hold an interchangeable instrument tip. The instrument tips may comprise scalers, excavators, explorers, probes, scrapers, or like instrument tips which are commonly used in dental procedures. Preferably, the collet or chuck reversibly engages a shank portion of the instrument tip, and can be tightened and loosened without requiring the use of a wrench or other tool. The instrument tips may alternatively comprise tissue grafters, biopsy samplers, or like medical endoscopic instruments. The reversible attachment means is preferably structured and configured so that the instrument tip, when fastened to the working end of the body, is generally aligned with the longitudinal axis of the body and connector so that dentists may handle the instrument holder in the same manner as conventional non-imaging hand instruments. The interchangeable instrument tips are preferably structured and configured such that the working portion of the tip generally terminates in the same position in space relative to the body of the instrument holder, so that the instrument tip, when installed, will always be centered and in focus with respect to the imaging optics.

The illumination transferring means preferably comprises two flexible incoherent fiberoptic bundles, although fused coherent fiberoptic bundles could alternatively be used. One such bundle is contained within the body, while the other is located within the connector. The fiberoptic bundle in the connector has a tight bundled end adjacent to the light source and a flared annular end adjacent to the swivel means, whereas the bundle in the body has a flared annular end adjacent to the swivel means and a pair of tight bundled ends adjacent to the working end of the body in a bifurcated configuration. The flared annular ends of the two bundles are coaxially aligned with the rotational axis of the body and connector, and thus are in optical communication when the body and connector are joined together to allow transfer of light therebetween. As an alternative to the bifurcated configuration of the fiberoptic bundle in the body, the head or working end can comprise a single tight bundled end. As a further alternative, the head end of the bundle in the body can be fashioned into a flared annular end, with the image transferring means coaxially aligned within the flared annular end.

The image transferring means preferably comprises a fused coherent fiberoptic bundle located in the body. One end of the fiberoptic bundle is situated adjacent to the working end of the body to receive images from a work area, and the other end is positioned adjacent to the coupling end of the body and coaxially aligned with the rotational axes of the body and connector. The image transferring means projects the image into an open coaxial path in the connector. In the preferred embodiment, an objective lens is positioned in the body at the end of the bundle adjacent to the work area. The optical train in the body is preferably similar or identical to that required for use with a dental drill, and focused on the tip of the instrument with a relatively short depth of field. Each interchangeable instrument tip is designed so that the working portion of the tip (the point) terminates in the same position in space relative to the body, thereby being in exact focus and in the center of view of the imaging means. Preferably, a focusing lens is positioned in the connector at the coupling end ahead of the image detection means. Alternatively, the focusing lens can be positioned in the coupling end of the body. As a further alternative, a first focusing lens can be positioned in the coupling end of the body, and a second focusing lens positioned adjacent to the imaging means, with an imaging fiberoptic bundle located in the connector between the coupling end and the second focusing lens. With each of these configurations, images are transferred along a coaxial optical path to the imaging means, the coaxial path extending between the body and connector through the swivel means. In this regard, note that the imaging path passes through the coaxial opening in the flared ends of the fiberoptic bundles of the illumination transferring means.

Preferably the imaging means comprises a charge coupled device (CCD) camera. The CCD camera is typically interfaced with an external image processor unit and video display whereby dental operations may be observed by dentist and patient, or medical procedures may be observed by physicians and other medical personnel. Data storage means may be included to store images from dental operations for later reference.

The swivel means for rotatably coupling the body and connector of the apparatus generally comprises a spool and spool body, with the spool located at the coupling end of the connector and the spool body located at the coupling end of the body. Alternatively, the placement of the spool and spool body could be reversed. The spool and spool body are coaxial with the rotational axis of the body and connector, with the spool engaging the spool body in a male-female configuration. Compressed air, water, and other fluid (gas or liquid) paths in the body are interfaced respectively with like paths in the connector via the spool body and spool by conventional means. The spool body allows air, water and other fluid paths to remain in flow communication while the body is swiveling or rotating relative to the connector. The image and illumination transferring means are preferably coaxial at the coupling ends of the body and connector, and preferably pass through the spool and spool body arrangement.

The image and illumination transfer means as related above may also be employed in an apparatus without a swivel feature. In such a case, the illuminating fiber optic bundle pieces and the imaging bundle and optical paths do not require any coaxial location.

An object of the invention is to provide an instrument holder apparatus having integrated intra-cavity camera or imaging capability.

Another object of the invention is to provide an instrument holder apparatus which can interchangeably receive and hold one of a plurality of various instrument tips.

Another object of the invention is to provide an instrument holder apparatus which allows swivel motion of a handle body relative to a connector.

Another object of the invention is to provide an instrument holder apparatus wherein the handle body may be quickly disconnected from the connector and interchanged.

Another object of the invention is to provide an instrument holder apparatus which allows delivery of water and/or pressurized air to the detachable instrument tip and work area.

Another object of the invention is to provide an instrument holder apparatus which can be disconnected for sterilization.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 5 is a bottom plan view of a bifurcated fiber optic cable employed as a first fiberoptic illumination bundle in the body portion of the invention shown in FIG. 2 and FIG. 4.

FIG. 6 is an end view of the flared annular end of the fiber optic cable shown in FIG. 5.

FIG. 7 is a perspective view of an annular fiber optic cable employed as a second fiberoptic illumination bundle in the connector portion of the invention shown in FIG. 3.

FIG. 8 is a side elevation view in partial cutaway of a preferred arrangement of imaging and illuminating fiberoptic bundles in the body shown in FIG. 2.

FIG. 9 is a side elevation view of a preferred arrangement for an illuminating fiberoptic bundle and imaging optical path and lens in the connector shown in FIG. 3.

DESCRIPTION OF THE PREFERRED EMBODIMENTS

Referring more specifically to the drawings, for illustrative purposes the present invention is embodied in the apparatus generally shown in FIG. 1 through FIG. 9. It will be appreciated that the apparatus may vary as to configuration and as to details of the parts without departing from the basic concepts as disclosed herein. Additionally, the invention is shown and described generally for use with interchangeable instrument tips of the type used in the dental profession. However, it should be readily apparent to those skilled in the art that the invention may also be utilized with instrument tips employed in medical, veterinary, and other clinical professions.

Figure 1:
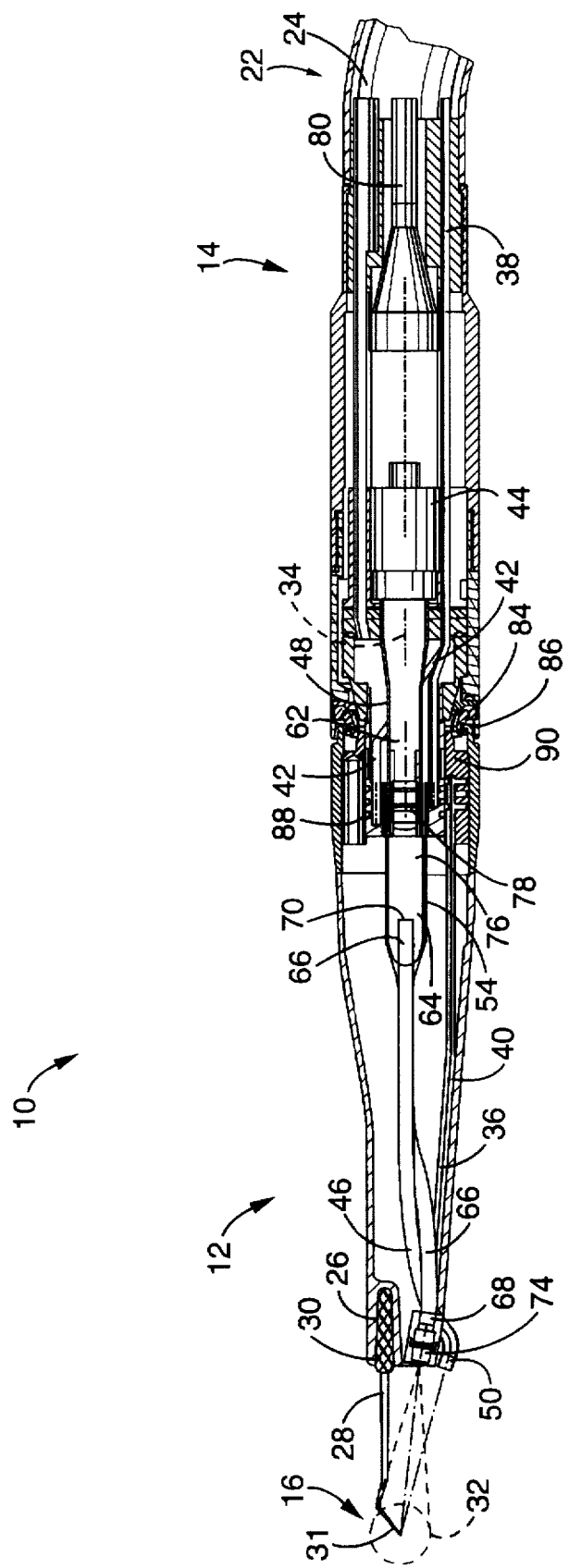
FIG. 1 is side elevation view in cross-section of a dental/medical instrument holder in accordance with the present invention, shown with an interchangeable instrument tip attached.
Figure 2:
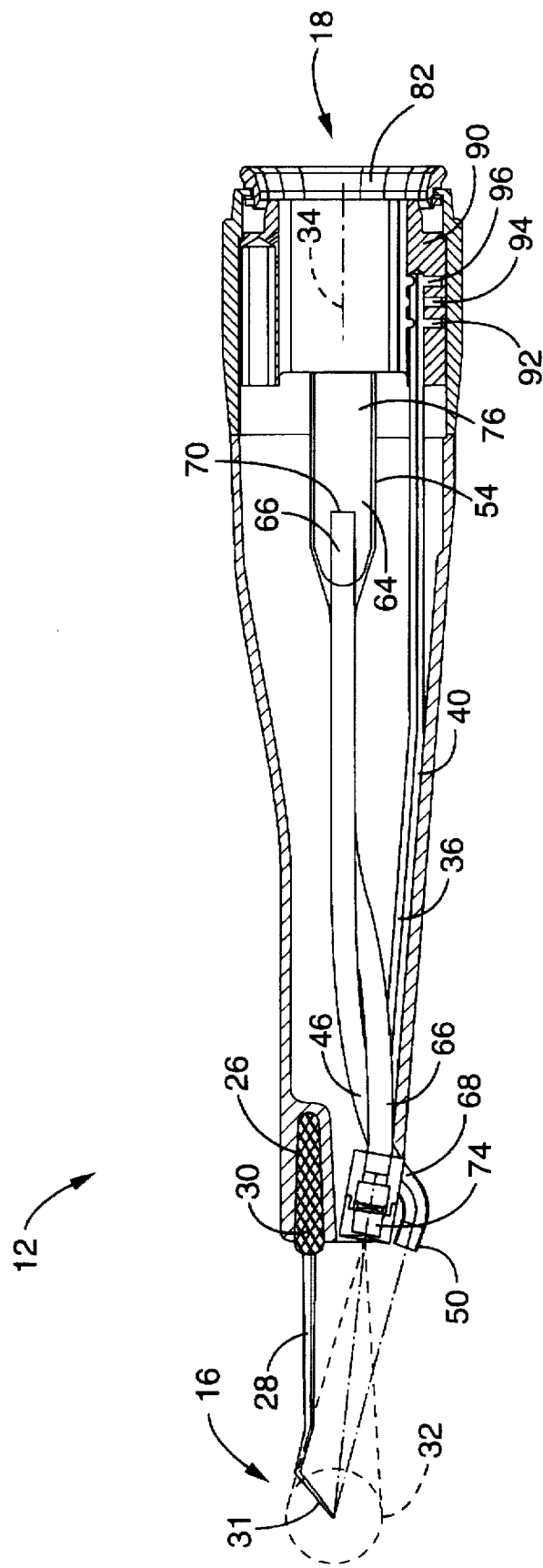
FIG. 2 is a side elevation view in cross-section of the body portion of the dental/medical instrument holder of FIG. 1.

Referring first to FIG. 1 through FIG. 4, a dental/medical instrument holder apparatus 10 in accordance with the present invention is generally shown. Dental/medical instrument holder 10 generally comprises an elongated handle or body member 12, and an elongated connector member or portion 14. Body 12 includes a first or working end 16, and a second or connecting end 18 (FIG. 2). Connector 14 includes a first or connecting end 20 (FIG. 3), and a second or distal end 22. Second end 18 of body 12 is reversibly coupled to first end 20 of connector 14, as discussed below in more detail. A supply cable 24 is coupled to second end 22 of connector 14.

Means for reversibly attaching instrument tips to instrument holder 10 are associated with first end 16 of body 12 as shown. The attachment means preferably comprises a sleeve, collar or collet 26 which slidably receives and holds an interchangeable and replaceable instrument tip 28. Instrument tip 28 may comprise, for example, a scaler, excavator, explorer, probe, scraper, or like instrument commonly used in the dental profession. Preferably, instrument tip 28 includes a shank portion 30, which may be tapered in shape as shown, with collet 26 structured and configured to reversibly engage shank portion 30 by friction, snap-fitting, quick-disconnect, or other conventional means. Instrument tip 28 and shank portion 30 preferably can be installed into and removed from collet 26 by hand, without requiring a wrench or other tool. Each interchangeable instrument tip 28 is preferably structured and configured so that the working portion 31 of the instrument tip 28, when installed on body 12, is in focus and centered with respect to the imaging optics discussed below. The non-working or shank portion 30 of each interchangeable instrument tip 28 are identically structured and configured to allow quick interchange or replacement of instrument tips 28.

The reversible attachment means 26 of the invention may alternatively comprise a chuck arrangement wherein a collar is tightened or loosened in order to install and remove instrument tip 28. Other standard arrangements for interchangeably receiving and holding instrument tip 28 may also be employed with the invention. Positioning means (not shown) for positionally adjusting instrument tip 28 within work area 32 may additionally be employed with the invention in conjunction with the attachment means 26 and working end 16 generally. The positioning means may comprise a translational screw adjuster or like quick-adjust positioning means. The positioning means would be used for optimizing the centering and focusing individual instrument tips 28 with the imaging optics discussed below.

The reversible attachment means 26 is preferably structured and configured such that instrument tip 28 is substantially co-linear with the longitudinal axis 34 of instrument holder 10, which is co-linear with the rotational axis of body 12, as discussed below. In this arrangement, the instrument holder 10 may be handled in the same manner as standard dental instruments. The reversible attachment means may alternatively be structured and configured to hold instrument tip 28 at an angle relative to longitudinal axis 34.

The invention preferably includes means for delivering, supplying or providing water and/or pressurized air to work area 32 and instrument tip 28. The water delivery means preferably comprises a water line or path 36 in body 12 and a water line or path 38 in connector 14, with water line 36 being generally in flow communication with water line 38 when body 12 is coupled to connector 14, as discussed below. Water line 36 connects with a nozzle (not shown) adjacent working end 16 of body 12, which directs water to work area 32 as required. The air delivery means of the invention preferably comprises an air line 40 in body 12 which communicates with air line 42 in connector 14 when body 12 and connector 14 are coupled together. Air line 40 connects with a nozzle (not shown) adjacent working end 16 of body 12, which directs air to work area 32 as required. Air line 40 and water line 36 may communicate with a shared nozzle or adjacent nozzles to provide air/water sprays or mixes. Supply hose 24 includes suitable conduits (not shown) which interface with water line 38 and air line 42, and which provide water and air respectively thereto. Water lines 36, 38 and air lines 40, 42 may comprise tubes, ducts, channels, or like features suitable for transporting water and air through body 12 and connector 14. The air and water delivery means of the invention allow instrument holder 10 to serve as a replacement for the standard dental air/water syringe used in most dental procedures. Thus, the invention eliminates the need for an air/water syringe as well as provides for the use of various instrument tips 28 interchangeably, thereby eliminating the need for multiple specific instruments and holders.

Connector 14 is preferably the same type of connector used for attachment of high speed and low speed dental handpieces which have air driven turbines. Connector 14 thus generally includes lines or paths (not shown) which can provide for drive air for a rotor or turbine of a handpiece, and for removing exhaust air from the same. The body 12 of instrument holder 10 may thus be used interchangeably with handpieces by coupling to the same connector as the handpiece.

Imaging means are provided with the present invention to allow the dentist and patient to view tool 28 and work area 32 during dental operations. Preferably, the imaging means comprises a CCD camera 44 or other solid state imaging device or any imaging means commonly used in the endoscopy art. A CCD camera 44 is shown integrated within connector 14, but may alternatively be located remotely from instrument holder 10 and receive images therefrom by fiberoptic or other conventional image transmission means. An image processor (not shown) may also be included. CCD camera 44 is interfaced by suitable means to a remote video display or TV monitor (not shown) whereby dental operations may be observed. Data storage means (not shown) and image printing means (not shown) may be included to store images from dental operations for later reference.

In the preferred embodiment, water delivery line or path 38 is arranged within connector 14 so that water provides cooling to CCD camera 44. Providing cooling to CCD camera 44 will improve the signal to noise ratio and increase the quality of the image, as well as increase the useful life of the camera. Other fluid paths (not shown) within connector 14, which may be used in association with a high or low-speed handpiece are also preferably positioned to provide cooling to CCD camera 44.

The invention includes illumination transferring means for transferring illumination from a light source to instrument tip 28 and work area 32, and image transferring means for transferring images from instrument tip 28 and work area 32 to an imaging means such as CCD camera 44. Referring more particularly to FIG. 5 through FIG. 7, as well as FIG. 1 through FIG. 4, the illumination transferring means preferably comprises a first illuminating fiberoptic bundle 46 in body 12, and a second illuminating fiberoptic bundle 48 in connector 14. First and second illuminating bundles 46, 48 are preferably flexible, incoherent type fiberoptic bundles, but could alternatively be a fused coherent fiberoptic bundle. As can be seen most clearly in FIG. 5, first illuminating bundle 46 includes a first illumination branch 50 and a second illumination branch 52 forming or defining a bifurcated end, and a flared annular end 54 opposite illumination branches 50, 52. Referring to FIG. 7, second illuminating bundle 48 includes a flared annular end 56 and a tight bundled or solid end 58. The individual optical fibers 60 in bundle 48, which are bunched together at solid end 58, are positionally rearranged along the length of bundle 48 to form a circular or annular arrangement of optical fibers 60 at annular end 56, thereby defining a channel or cavity 62 within annular end 56. Similarly, the individual optical fibers (not shown) in first illuminating bundle 46 are positionally rearranged along the length of bundle 46 from an annular arrangement at annular end 54 into the bifurcated illumination branches 50, 52. A channel or cavity 64 is generally defined within annular end 54. Solid end 58 of second illuminating bundle 48 is interfaced or coupled with a light source, such as a light bulb or other fiberoptic illumination source (not shown) in connector 14 or supply hose 24. It will be appreciated that the light appreciated that the light source could be located either within body 12 or connector 14 if desired. For example, the light source could be a small bulb which is located within the body 12 and which is in dynamic contact with the connector 14 to power the bulb.

First illuminating bundle 46 is positioned within body 12, and second illuminating bundle 48 is positioned within connector 14, so that annular end 54 of first illuminating bundle 46 is positioned adjacent second end 18 of body 12, and annular end 56 of second illuminating bundle 48 is positioned adjacent first end 20 of connector 14. Annular ends 54, 56 of first and second bundles 46, 48 respectively are positioned so that they are aligned and optically interface with each other when body 12 and connector 14 are coupled together. Note, however, that the annular ends do not touch so as not to introduce rotational drag. This configuration allows illumination received from solid end 58 of second illuminating bundle 48 to transfer or travel from annular end 56 to annular end 54, and hence to first and second illumination branches 50, 52 of first illuminating bundle 46. First and second illumination branches 50, 52 are positioned adjacent body first end 16, and provide dual lighting to instrument tip 28 and work area 32. This preferred dual lighting arrangement reduces shadows and optimizes images received from work area 32. Preferably, annular ends 54, 56 of first and second illumination bundles 46, 48 are positioned coaxially relative to the rotational axis (also the longitudinal axis) 34 of body 12 and connector 14, as shown in FIG. 1 through FIG. 4, so that the relative position and orientation of annular ends 54, 56 will remain fixed during rotational or swiveling motion of body 12 relative to connector 14, allowing illumination transfer during the swivel motion. In other words, when the optical axes of first and second illuminating bundles 46, 48 are coaxial with the rotational axis 32 of body 12 and handpiece 14, uninterrupted illumination transfer occurs over 360 degrees of rotation.

Referring more particularly to FIG. 8 and FIG. 9 as well as FIG. 1 through FIG. 4, the preferred image transferring means of the invention is generally shown together with the illumination transferring means. The image transferring means generally comprises a fiberoptic imaging bundle 66 included in body 12. Imaging bundle 66 is preferably a fused coherent fiberoptic bundle, but could alternatively be a flexible coherent fiberoptic bundle provided that image alignment can be maintained. Imaging bundle 66 has a first end 68 positioned adjacent working end 16 of body 12, and a second end 70 positioned adjacent body second end 18. Imaging 66 bundle has an optical axis 72 (FIG. 8), and ends 68, 70 of bundle preferably have surfaces which are perpendicular to the optical axis 72. Note also that the second end 70 of imaging bundle 66 is longitudinally offset from the coupling end 18 of body 12 so as to prevent interference from any light leakage at the flared annular ends of the illumination bundles 46, 48.

An objective lens system 74 is included at first end 68 of imaging bundle 66, and is positioned to receive images from work area 32. Focusing means (not shown) for positionally adjusting objective lens system 74 relative to the working portion of instrument tip 31 and work area 32 are preferably included with objective lens system 74. An imaging window (not shown) may be included on imaging bundle second end 70, and a protective window (not shown) may also be included adjacent lens system 74 to protect lens system 74 from water spray from work area 32 while allowing transmission of images therethrough. A protective window (not shown) is also preferably included on focusing lens system 78.

The image transferring means projects images along an optical path 76, which extends between body 12 and connector 14. Images received by objective lens 74 are transmitted through imaging bundle 66 and along optical path 76 to CCD camera 44. Optical path 76 preferably resides within the channels or hollow portions 62, 64 defined by annular ends 54, 56 of first and second illuminating bundles 46, 48. Optical path 76 is preferably coaxial with longitudinal or rotational axis 34 and CCD camera 44, so that when body 12 and connector 14 are coupled together, images from imaging bundle 66 are transferred along optical path 76. Optical path 76 is coaxial with rotational axis 34, so that images may be transmitted from imaging bundle 66 along optical path 76 during rotational motion of body 12 relative to connector 14 without interruption or distortion of images.

A focusing lens system 78 is positioned in connector 14 along optical path 76 between CCD camera 44 and second end 70 of imaging bundle 66. Referring to FIG. 9, lens system 78 may be included at any point along optical path 76, and is preferably located along optical path 76 within channel 62 at annular end 56 of second illuminating bundle 48 in connector 14. Lens system 78 is coaxial with optical path 76 and rotational axis 34 of body 12 and connector 14. Lens system 78 generally includes conventional optics for fiberoptic transmission, such as a field flattener and a plurality of doublet lenses. Lens system 78 may alternatively be located in body 12 within cavity 64 in the annular end 54 of illumination bundle 46, and along optical path 76 adjacent to second end 70 of imaging bundle 66. Or, a second imaging bundle (not shown) can be included in connector 14 along optical path 76 between lens system 78 and the end of the connector. Those skilled in the art will appreciate that other lens placements are possible. While the optical medium along optical path 76 is preferably air, it is contemplated that vacuum, liquids, fused glass, or other optical media capable of transferring images may comprise the optical medium along optical path 76.

It should be readily apparent to persons skilled in the art that the image and illumination transferring means related herein are but a few of many ways and configurations by which images may be transferred from instrument tip 28 and work area 32 to CCD camera 44, and illumination transferred from a light source to instrument tip 28. A plurality of suitably oriented lenses and mirrors along an optical path extending from an area adjacent first end 16 of body 12 to CCD camera 44 could also serve as transferring means for images and illumination without the use of fiber optic bundles. The illumination means could be a light source adjacent to instrument tip 28 and work area 32, or could be included within body 12 and transferred by fiberoptic or other means to work area 32 and instrument tip 28, or the illuminating means could be located remotely and transferred by fiberoptic illuminating bundles 46, 48 as related above. CCD camera 44 is shown generally in FIG. 1 and FIG. 4 as housed coaxially within connector 14, and communicating with a remote video monitor or other display means (not shown) via video link 80 or other electronic or optical communication channel in supply cable 24. CCD camera 44 may alternatively be placed off-center within connector 14, with the image transferring means including mirrors or additional fused or flexible fiberoptic bundles to direct images to CCD camera 44. Other fiber optic bundle arrangements may be used alternatively or in addition to those related above. For example, optical path 76 may alternatively comprise a pair of flexible or fused fiber optic bundles which are interfaced at the junction of body 12 and connector 14. Generally, if body 12 and connector 14 are coupled together in a swiveling relationship, the image and illumination transferring means will require some coaxial components adjacent the junction of body 12 and connector 14 to allow continuous transfer of images and illumination while body 12 and connector 14 rotate relative to each other. If body 12 and connector 14 are coupled together in a fixed or non-swiveling relationship, the image transferring means and illumination transferring means will not require coaxial components.

Figure 3:
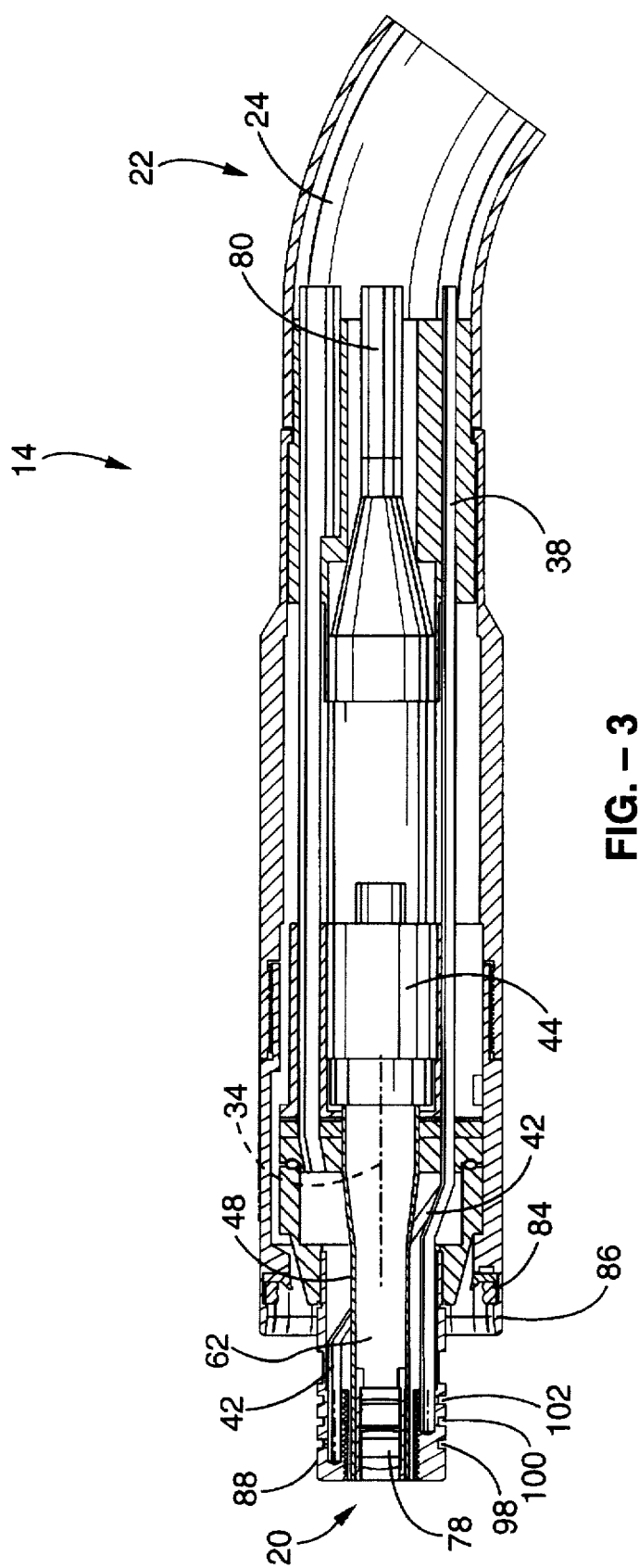
FIG. 3 is a side elevation view in cross-section of the connector portion of the dental/medical instrument holder of FIG. 1.
Figure 4:
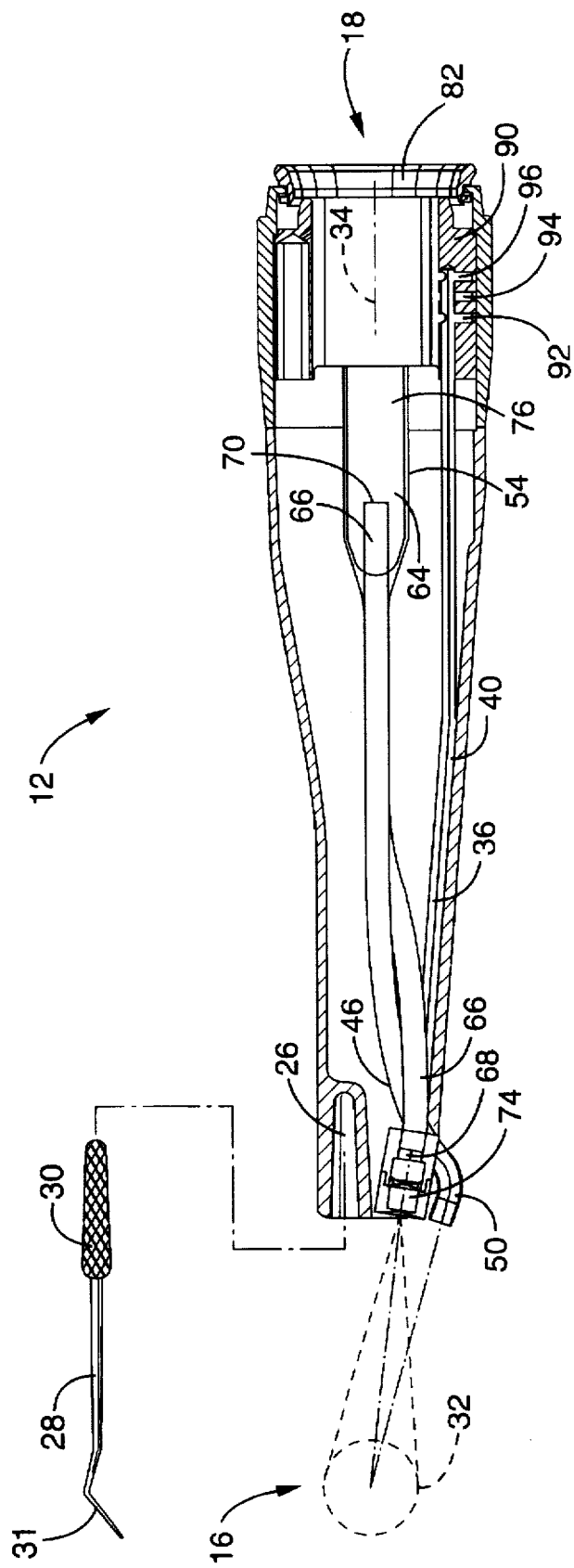
FIG. 4 is a side elevation view in cross-section of the body portion of FIG. 2 shown with the instrument tip detached.

Referring again to FIG. 1 through FIG. 4, the invention preferably includes swivel means for rotatably coupling body 12 to connector 14, so that body 12, and thus instrument tip 28, may be moved 360 degrees relative to connector 14 and supply cable 24. The swivel means preferably comprises an annular swivel ring 82 (FIG. 2, FIG. 4) adjacent second end 18 of body 12, which reversibly engages a snap-on ring 84 (FIG. 3) on connector first end 20 which is contained generally within an encircling flange 86 (FIG. 3). Swivel ring 82 and snap-on ring 84 engage or couple in a manner which allows facile rotation or swiveling of body 12 relative to connector 14.

The swivel means also comprises a spool 88 on connector first end 20 which rotatably engages a spool body 90 on body second end 18 when connector 14 and body 12 are joined together. Spool 88 could alternatively be included on body second end 18, with spool body placed on connector first end 20. Spool 88 and spool body 90 are shown with a structure and configuration suitable for use with a dental handpiece as well as the instrument holder 10, with a plurality of inwardly disposed lateral channels 92, 94, and 96 (FIG. 2, FIG. 4) included in spool body 90, and a plurality of outwardly disposed lateral channels 98, 100, and 102 (FIG. 4) included in spool 88. When spool 88 and spool body 90 are engaged, channels 92, 94, 96 in spool body 90 are aligned with channels 98, 100, 102 respectively of spool 88, so that a plurality of internal lateral passages (not shown) are formed between spool 88 and spool body 90. Water lines 36, 38 and air lines 40, 42 remain in flow communication during rotational motion of body 12 relative to connector 14 through the passages thus formed by the engaging or coupling of spool 88 and spool body 90. As related above, the connector 14 of the invention preferably can be used with dental handpieces as well as instrument holder body 12, and thus spool 88 and spool body 90 include a larger number of channels than are required for connecting water lines 36, 28 and air lines 40, 42, with the additional channels being used for the drive air and/or exhaust air for dental handpiece turbines. It should be readily apparent to persons of ordinary skill in the art that many possible arrangements are possible within spool 88 and spool body 90 for providing flow communication of air and water lines during rotational motion, and the arrangement shown in FIG. 1 through FIG. 4 is but one of many possibilities within the scope of the present invention.

The image and illumination transferring means preferably pass through spool 88 and spool body 90. The annular end 56 of second illuminating fiberoptic bundle 48 passes through spool 88, and lens system 78 is located therewithin. Annular end 54 of first illuminating fiberoptic bundle 46 is coaxially positioned in body 12 relative to spool body 90, so that annular end 54 will interface with annular end 56 of second illuminating bundle 48 when spool 88 and spool body 90 are engaged. When spool 88 and spool body 90 are engaged, images from imaging bundle 66 are transmitted along optical path 76 through spool 88 and spool body 90 to CCD camera 44. Thus, image and illumination transfer, as well as compressed air and water supply, are not interrupted by rotational motion of body 12 relative to connector 14 during dental procedures. The swivel means allows easy manipulation of the handpiece 10 and produces little or no stress on the hand of a dentist using the invention. The swivel feature of the invention also allows quick disconnection of body 12 from connector 14, and replacement with a different instrument. All of the components included in body 12 are preferably made of materials which can be heat sterilized by autoclaving or other means.

The swivel connection of the present invention makes it easier for a dentist to identify a tooth and orient the handpiece than is possible in conventional dental/medical tools with imaging systems, although it will be appreciated that the swivel means can be eliminated if desired. The present invention provides a true representation of instrument tip to tooth orientation, and a dentist using the invention can use the orientation or position of instrument tip 28 on the video screen as a pointer since it will always be in view.

When the body 12 of the invention is positioned with working end 16 and instrument tip 28 pointing towards a particular tooth, the image relayed by the invention to a video monitor is the true representation of the orientation of instrument tip 28 relative to the tooth. Rotation of body 12 relative to connector 14 results in a corresponding rotation of the screen image, maintaining a video image of the true orientation of instrument tip 28 and tooth. The instrument tip 28 is in view at all times, and follows the movement of handpiece 10. The instrument tip 28 may thus be used as a pointer or positioning guide when using the invention. The patient as well as the dentist may view the procedure with the present invention. As mentioned above, each interchangeable instrument tip 28 is preferably structured and configured so that the working portion 31 of the instrument tip 28, when installed in collet 26, is in focus and centered with respect to objective lens system 74 and the imaging optics generally of the invention.

During a typical dental procedure wherein instrument holder 10 is employed, a variety of instrument tips 28 would generally be available at the work site. If a change in instrument tip 28 is required during a procedure, the dentist merely disengages the instrument tip 28 from collet 26 and exchanges a new instrument tip 28 therefor. Preferably, the interchangeable instrument tips are constructed of heat sterilizable materials. Instrument tips 28 should be more economical to purchase and replace (when dull or worn) than the currently available hand instruments due to their small size and absence of a handle. Alternatively, instrument tips 28 may be produced from inexpensive materials with the intent of being for single patient use and disposable, thereby eliminating the need for heat sterilization between uses.

The instrument holder 10 comprising the present invention may in many cases eliminate the need for the typical dental air/water syringe. Activation of air, water or air/spray mixture could be accomplished by depression of a foot control as used to activate air and/or water spray for a dental drill. Alternatively, supply cable 24 could be coupled to a dental unit supplying pressurized air and water and activated by switches like those utilized on common dental air/water syringe devices. The switches may be incorporated into body 12 or connector 14 to afford activation of air, water or air/water spray as required by persons using the invention.

Accordingly, it will be seen that this invention provides an instrument holder apparatus with integrated imaging capability and swivel movement and which allows interchangeable use of multiple instrument tips. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A dental/medical instrument, comprising:
   (a) a body member, said body member including a first end and a second end;
   (b) a connector member, said connector member having a first end and a second end;
   (c) coupling means for detachably coupling said second end of said body member to said first end of said connector member;
   (d) means for reversibly attaching an instrument tip to said first end of said body member;
   (e) illumination transferring means for transferring illumination from a light source to a work area adjacent said instrument tip; wherein said illumination transferring means extends though said body member and said connector member, said illumination transferring means including opposing annular ends adjacent said coupling means, said opposing annular ends having a coaxial opening therethrough;
   (f) image transferring means for transferring an image of said work area; and wherein said imaging means transfers images though an optical path extending through said coaxial opening in said illumination transferring means; and
   (g) imaging means for detecting said image for visual display or recording thereof.

2. A dental/medical instrument as recited in claim 1, further comprising means for delivering water to said work area.

3. A dental/medical instrument as recited in claim 1, further comprising means for delivering pressurized air to said work area.

4. A dental/medical instrument as recited in claim 1, wherein said coupling means includes swivel means for rotatably coupling said body member to said connector member.

5. A dental/medical instrument as recited in claim 4, wherein said body member and said connector member have a common rotational axis, said annular ends of said illumination transferring means positioned coaxially with said rotational axis adjacent said swivel means, said imaging means positioned coaxially with said rotational axis adjacent said swivel means, and said optical path positioned coaxially with said rotational axis adjacent said swivel means.

6. A dental/medical instrument, comprising:
   (a) a body member, said body member including a first end and a second end;
   (b) a connector member, said connector member having a first end and a second end;
   (c) coupling means for detachably coupling said second end of said body member to said first end of connector member;
   (d) mean for reversibly attaching an instrument tip to said first end of said body member;
   (e) illumination transferring means for transferring illumination from a light source to a work area adjacent said instrument tip, wherein said illumination transferring means extends through said body member and said connector member, said illumination transferring means including opposing annular ends adjacent said coupling means, said opposing annular ends having a coaxial opening therethrough;
   (f) image transferring means for transferring an image of said work area and a working portion of said instrument tip, wherein said imaging means transfers images through an optical path extending through said coaxial opening in said illumination transferring means; and
   (g) imaging means for detecting said image for visual display or recording thereof.

7. A dental/medical instrument as recited in claim 6, further comprising:
   (a) means for delivering water to said work area; and
   (b) means for delivering pressurized air to said work area.

8. A dental/medical instrument as recited in claim 6, wherein said illumination transferring means comprises:
   (a) a first illuminating fiberoptic bundle, said first illuminating bundle included in said body member, said first illuminating bundle having a first end, and an annular second end, said first end positioned adjacent said first end of said body, said annular second end positioned adjacent said second end of said body member; and
   (b) a second illuminating fiberoptic bundle, said second illuminating bundle included in said connector member, said second illuminating bundle including a first annular end positioned adjacent said first end of said connector, said second illuminating bundle including a bundled end, said bundled end configured for receiving light from said light source.

9. A dental/medical instrument as recited in claim 6, wherein said image transferring means comprises an imaging fiber optic bundle, said imaging bundle included in said body member, said imaging bundle having a first end positioned adjacent said first, end of said body member, said imaging bundle having a second end adjacent said second end of said body member.

10. A dental/medical instrument as recited in claim 6, further comprising swivel means, included with said coupling means, for rotatably coupling said body member to said connector member.

11. A dental/medical instrument as recited in claim 10, wherein swivel means comprises a spool and a spool body, said spool engaging said spool body, said spool and said spool body positioned coaxially with a rotational axis of said body member and said connector member, said rotational axis coaxial with said longitudinal axis.

12. A dental/medical instrument as recited in claim 11, wherein said annular end of said first illuminating bundle is positioned coaxially with said rotational axis, said annular end of said second illuminating bundle is positioned coaxially with said rotational axis, said first end of said imaging bundle is positioned coaxially with said rotational axis, and said optical path is positioned coaxially with said rotational axis.

13. A dental/medical instrument, comprising:
   (a) a body member, said body member including a first end and a second end;
   (b) a connector member, said connector member having a first end and a second end;
   (c) coupling means for detachably coupling said second end of said body member to said first end of said connector member;
   (d) means for reversibly attaching an instrument tip to said first end of said body member;
   (e) illumination transferring means for transferring illumination from a light source to a work area adjacent said instrument tip, wherein said illumination transferring means extends through said body member and said connector member, said illumination transferring means including opposing annular ends adjacent said coupling means said opposing annular ends having a coaxial opening therethrough;
   (f) image transferring means for transferring an image of said work area, wherein said imaging means transfers images through an optical path extending through said coaxial opening in said illumination transferring means;
   (g) imaging means for detecting said image for visual display or recording thereof;
   (h) means for delivering water to said work area; and
   (i) means for delivering pressurized air to said work area.

14. A dental/medical instrument as recited in claim 13, wherein:
   (a) said illumination transferring means comprises a first illuminating fiberoptic bundle, said first illuminating bundle included in said body member, said first illuminating bundle having a first end and an annular second end, said first end positioned adjacent said first end of said body, said annular second end positioned adjacent said second end of said body member, said illumination transferring means further comprising a second illuminating fiberoptic bundle, said second illuminating bundle included in said connector member, said second illuminating bundle including a first annular end positioned adjacent to said first end of said connector, said second illuminating bundle including a bundled end, said bundled end configured for receiving light from said light source; and
   (b) said image transferring means comprises an imaging fiber optic bundle, said imaging bundle included in said body member, said imaging bundle having a first end positioned adjacent to said first end of said body member, said imaging bundle having a second end adjacent said second end of said body member.

15. A dental/medical instrument as recited in claim 14, further comprising:
   (a) first lens means for directing images to said image transferring means, said first lens means positioned in said body member adjacent to said first end of said image transferring means; and
   (b) second lens means for directing images from said image transferring means to said imaging means.

16. A dental/medical instrument as recited in claim 14, wherein said annular end of said first illuminating bundle is positioned coaxially with said rotational axis, said annular end of said second illuminating bundle is positioned coaxially with said rotational axis, said first end of said imaging bundle is positioned coaxially with said rotational axis, and said optical path is positioned coaxially with said rotational axis.

17. A dental/medical instrument as recited in claim 13, wherein said coupling means includes swivel means for rotatably coupling said body member to said connector member, said swivel means including a spool, said swivel means including a spool body, said spool engaging said spool body, said spool and said spool body positioned coaxially with a rotational axis of said body member and said connector member, said rotational axis coaxial with said longitudinal axis, said water delivery means passing through said spool and said spool body, said compressed air delivery means passing through said spool and said spool body.

* * * * *

UNITED STATES PATENT AND TRADEMARK OFFICE
CERTIFICATE OF CORRECTION

PATENT NO. : 5,743,731
DATED : April 28, 1998
INVENTOR(S) : Craig J. Lares, Ravi Pathmanabhan and Jason E. Orgain It is certified that error appears in the above-identified patent and that said Letters Patent is hereby corrected as shown below:

Column 11,
Lines 47 and 54, change "though" to -- through --

Column 12,
Line 15, change "end of connector" to -- end of said connector --
Line 65, change "wherein swivel" to -- wherein said swivel --

Signed and Sealed this

Fourteenth Day of May, 2002

Attest:

JAMES E. ROGAN
Attesting Officer
Director of the United States Patent and Trademark Office